United States Patent
Lee et al.

(10) Patent No.: US 12,213,790 B2
(45) Date of Patent: Feb. 4, 2025

(54) RING-SHAPED BIOMETRIC SIGNAL SENSING DEVICE

(71) Applicant: SKY LABS INC., Seongnam-si (KR)

(72) Inventors: Byung Hwan Lee, Yongin-si (KR); Chang Hyun Baik, Suwon-si (KR); Dong Hyun Lee, Gunpo-si (KR)

(73) Assignee: SKY LABS INC., Seongnam-si (KR)

( * ) Notice: Subject to any disclaimer, the term of this patent is extended or adjusted under 35 U.S.C. 154(b) by 495 days.

(21) Appl. No.: 17/604,176

(22) PCT Filed: Mar. 18, 2020

(86) PCT No.: PCT/KR2020/003666
§ 371 (c)(1),
(2) Date: Oct. 15, 2021

(87) PCT Pub. No.: WO2020/218741
PCT Pub. Date: Oct. 29, 2020

(65) Prior Publication Data
US 2022/0192568 A1    Jun. 23, 2022

(30) Foreign Application Priority Data
Apr. 25, 2019 (KR) .......... 10-2019-0048569

(51) Int. Cl.
| | |
|---|---|
| A61B 5/256 | (2021.01) |
| A61B 5/00 | (2006.01) |
| A61B 5/021 | (2006.01) |
| A61B 5/024 | (2006.01) |
| A61B 5/24 | (2021.01) |
| A61B 5/28 | (2021.01) |

(52) U.S. Cl.
CPC .......... *A61B 5/256* (2021.01); *A61B 5/02141* (2013.01); *A61B 5/02438* (2013.01); *A61B 5/24* (2021.01); *A61B 5/28* (2021.01); *A61B 5/6826* (2013.01)

(58) Field of Classification Search
CPC . A61B 5/256; A61B 5/02141; A61B 5/02438; A61B 5/24; A61B 5/28; A61B 5/6826
See application file for complete search history.

(56) References Cited

FOREIGN PATENT DOCUMENTS

| EP | 3451117 A1 | * | 3/2019 | ......... A61B 5/02405 |
|---|---|---|---|---|
| KR | 20160029412 A | * | 3/2016 | ........... A61B 5/0531 |

* cited by examiner

*Primary Examiner* — Tammie K Marlen
*Assistant Examiner* — Maria Catherine Anthony
(74) *Attorney, Agent, or Firm* — Bridgeway IP Law Group, PLLC; Sang Ho Lee; Hyun Woo Shin

(57) ABSTRACT

A ring-shaped biometric signal sensing device according to an embodiment of the present invention comprises: a first electrode (10), which is provided in a ring shape, is formed of conductors, and is fitted on a user's finger so as to make contract with the finger; a second electrode (20), which is assembled on the outside of the first electrode (10), is formed of conductors, and makes contact with the user's body; an insulation unit (30), which includes the first electrode (10) and is insert-injected so as to maintain insulation between the first electrode (10) and the second electrode (20); and a control unit (40), which is arranged in the insulation unit (30), includes a biometric sensor, and collects biometric signals when the second electrode (20) makes contact with the user's body.

9 Claims, 6 Drawing Sheets

RING-SHAPED BIOMETRIC SIGNAL SENSING DEVICE

TECHNICAL FIELD

The present disclosure relates to a biometric signal sensing device for sensing and collecting a biometric signal such as an electrocardiogram and blood pressure.

BACKGROUND ART

In general, an electrocardiogram sensing device is an important tool widely used for clinical diagnosis of heart disease and can be used to diagnose symptoms such as myocardial infarction and pulmonary embolism.

In particular, people with or suspected of having heart disease need to detect or give early warning of sudden cardiac abnormalities.

The electrocardiogram sensing device attaches an electrode to the body and detects minute electrical signals generated when the heart beats.

Such a conventionally known electrocardiogram sensing device is inconvenient to wear because a device such as an electrode has a conspicuous size and is too large.

Conventionally, a wearable device for detecting biometric signals such as blood pressure has been proposed, and in this regard, most wearable deices are worn on the wrist, and since the wearable device does not have a configuration for allowing the device to come into contact with other body parts other than a body part on which the device is worn, the reliability of the electrocardiogram data is low.

In another aspect, when an electrocardiogram is measured, gel is applied to the body of a patient, which may cause discomfort to the patient.

PRIOR ART DOCUMENT

Patent Document (Patent Document 1) KR 10-1842915 B1
(Patent Document 2) KR 10-1798495 B1
(Patent Document 3) KR 10-1726613 B1
(Patent Document 4) US 2018/0020977 A1

Non-Patent Document (Non-patent Document 1) Design and implementation of real-time blood pressure measurement system using smartphone, Young-Jun Gil, Jeong-Tae Lee, ISSN 2383-6318 (Print)/ISSN 2383-6326 (Online), KIISE Transactions on Computing Practices, Vol. 21, No. 3, pp. 192-214, 2015. 3, http://dx.doi.org/10.5626/KTCP.2015.21.3.192

DISCLOSURE

Technical Problem

Therefore, the present disclosure has been made in view of the above problems, and it is one object of the present disclosure to provide a ring-shaped biometric signal sensing device for detecting an electrocardiogram and blood pressure.

It is another object of the present disclosure to provide a ring-shaped biometric signal sensing device worn on a finger and having an ultra-compact external size to minimize wearing discomfort.

Technical Solution

In accordance with one aspect of the present disclosure, provided is a ring-shaped biometric signal sensing device including a first electrode 10 provided in a ring shape, formed of a conductor, and put on a finger of a user to be in contact with the finger, a second electrode 20 assembled on an outside of the first electrode 10, formed of a conductor, and in contact with a body of the user, an insulating unit 30 molded with the first electrode 10 through insert injection and maintaining insulation between the first electrode 10 and the second electrode 20, and a controller 40 disposed in the insulating unit 30, including a biometric sensor, and configured to collect a biometric signal when the second electrode 20 comes into contact with the body of the user.

In the ring-shaped biometric signal sensing device according to an embodiment of the present disclosure, the biometric signal may be any one of an electrocardiogram signal, a blood pressure signal, and a pulse signal.

In the ring-shaped biometric signal sensing device according to an embodiment of the present disclosure, the controller 40 may include a communication terminal connected to a communication terminal and configured to transmit data of the biometric signal.

The controller 40 of the ring-shaped biometric signal sensing device according to an embodiment of the present disclosure may detect the biometric signal of the user or may transmit the collected data when the user repeats contact and release of the second electrode 20 once or twice in a row.

In the ring-shaped biometric signal sensing device according to an embodiment of the present disclosure, a rim 12 may be formed at an outer periphery of the first electrode 10, an insulating layer may be formed on the rim 12, and the first electrode 10 and the second electrode 20 may be insulated from each other through the insulating layer.

In the ring-shaped biometric signal sensing device according to an embodiment of the present disclosure, the insulating unit 30 may be formed of a flexible material, and a portion of the insulating unit 30 may be placed through the first electrode 10 to be close contact with the finger of the user.

Details of other embodiments are included in the detailed description and drawings.

Advantageous Effects

The ring-shaped biometric signal sensing device according to an embodiment of the present disclosure configured as above may detect a biometric signal such as an electrocardiogram and blood pressure.

The ring-shaped biometric signal sensing device according to an embodiment of the present disclosure may minimize wearing discomfort by providing an external size that is ultra-compact enough to be worn on the finger.

The ring-shaped biometric signal sensing device according to the embodiment of the present disclosure may improve the reliability of collected biometric signal by minimizing an error when a first electrode is securely attached to the finger of the user to secure the biometric signal.

The ring-shaped biometric signal sensing device according to the embodiment of the present disclosure may be more convenient for a patient because it is not necessary to apply gel or the like to the body of the patient when an electrocardiogram is measured.

BEST MODE

The attached drawings for illustrating exemplary embodiments of the present disclosure are referred to in order to gain a sufficient understanding of the present disclosure, the merits thereof, and the objectives accomplished by the implementation of the present disclosure.

Hereinafter, an embodiment of the present disclosure will be described in detail with reference to the accompanying drawings. It should be understood that the embodiments described below are illustratively shown to aid in understanding of the present disclosure, and that the present disclosure is implemented with various modifications different from the embodiments described herein. However, in the following description of the present disclosure, a detailed description of known functions and configurations incorporated herein will be omitted when it may make the subject matter of the present disclosure unclear. In addition, the accompanying drawings are not drawn to scale, but the size of some components may be exaggerated to aid in understanding of the invention.

Terms such as "first" and "second" are used herein merely to describe a variety of constituent elements, but the constituent elements are not limited by the terms. The terms are used only for the purpose of distinguishing one constituent element from another constituent element. For example, a first element may be termed a second element and a second element may be termed a first element without departing from the teachings of the present disclosure The terms used in the specification are defined in consideration of functions used in the present disclosure, and can be changed according to the intent or conventionally used methods of producers. Accordingly, definitions of the terms should be understood on the basis of the entire description of the present specification.

Like reference numerals in the specification denote like elements.

Figure 1:
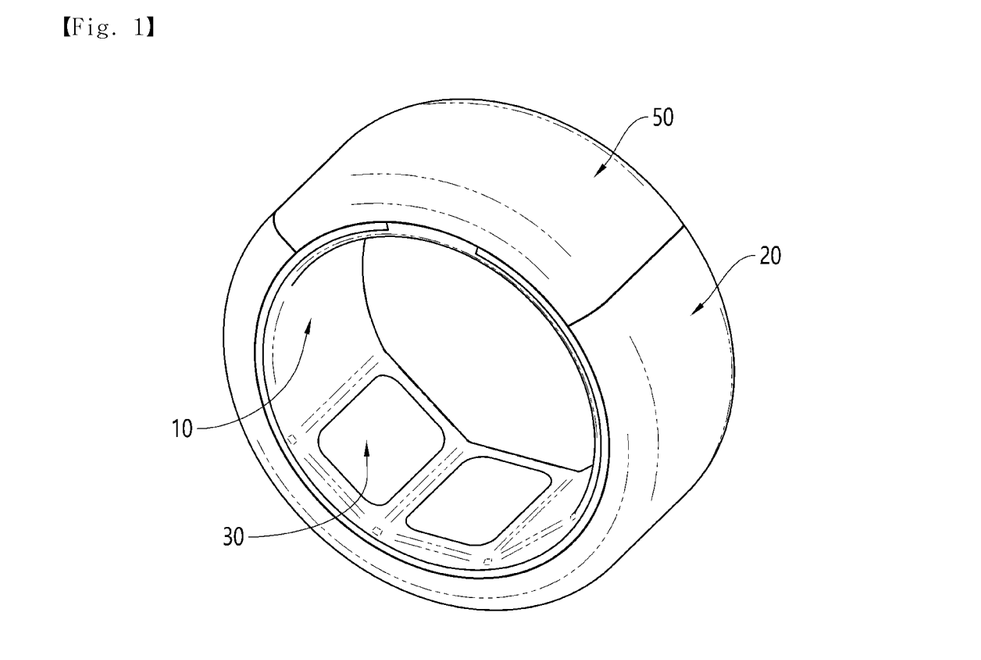
FIG. 1 is a diagram for explaining a ring-shaped biometric signal sensing device according to an embodiment of the present disclosure.
Figure 2:
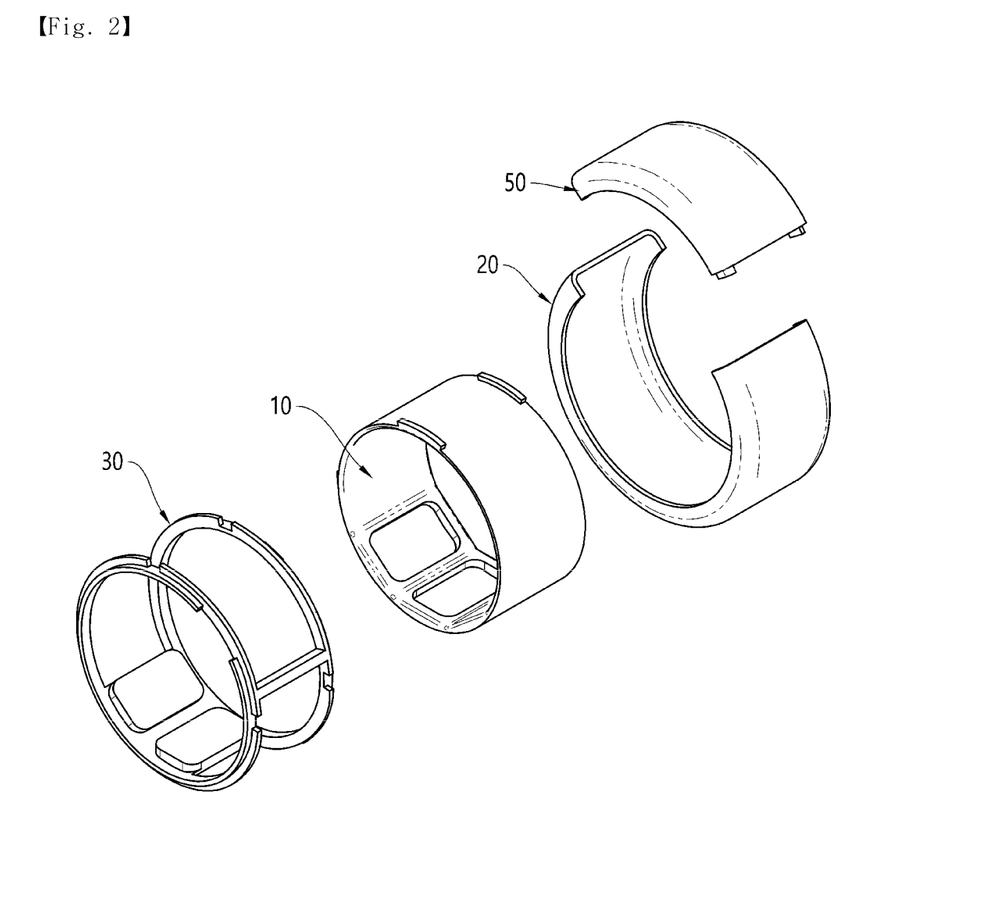
FIG. 2 is a diagram for explaining main components of a ring-shaped biometric signal sensing device according to an embodiment of the present disclosure.
Figure 3:
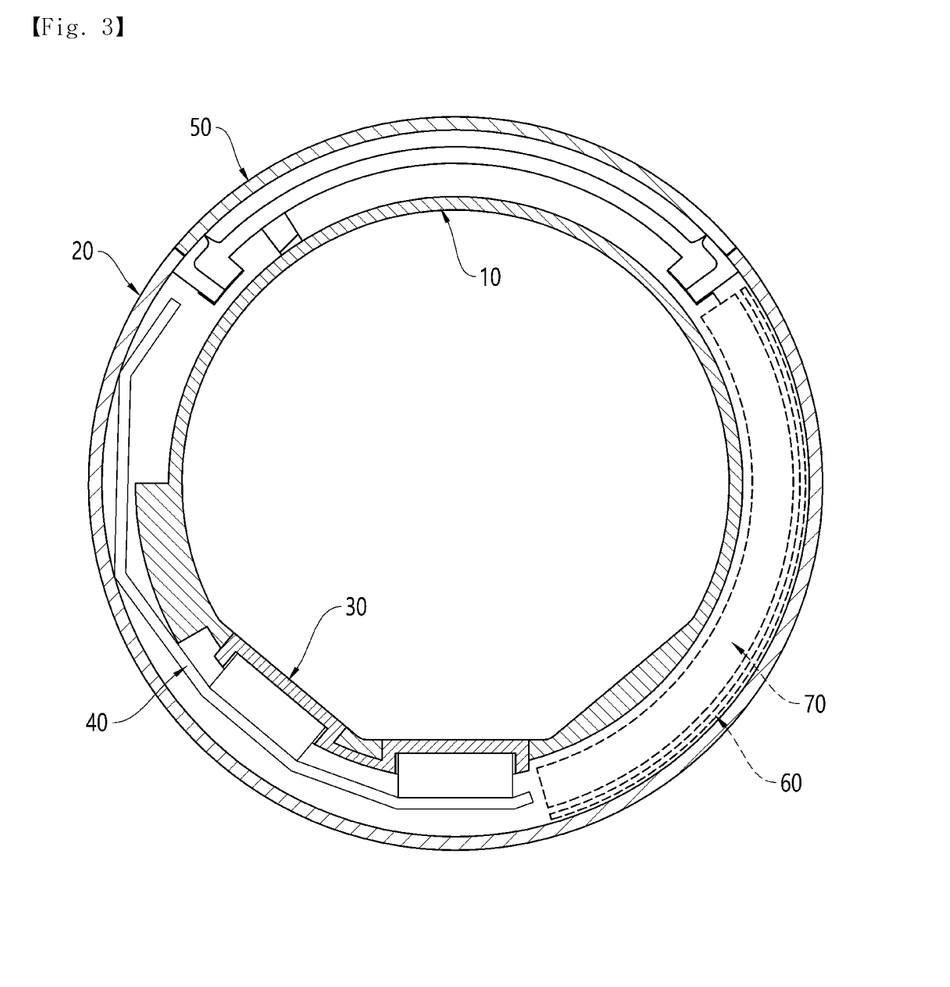
FIG. 3 is a cross-sectional view for explaining the internal configuration of a ring-shaped biometric signal sensing device according to an embodiment of the present disclosure.

Hereinafter, a ring-shaped biometric signal sensing device according to an embodiment of the present disclosure will be described with reference to FIGS. 1 to 3. FIG. 1 is a diagram for explaining a ring-shaped biometric signal sensing device according to an embodiment of the present disclosure. FIG. 2 is a diagram for explaining main components of a ring-shaped biometric signal sensing device according to an embodiment of the present disclosure. FIG. 3 is a cross-sectional view for explaining the internal configuration of a ring-shaped biometric signal sensing device according to an embodiment of the present disclosure.

DESCRIPTION OF REFERENCE NUMERALS

10, 20: first and second electrodes 30: insulating unit
40: top cover 50: controller
60: printed circuit board 70: battery

Mode for Invention

A ring-shaped biometric signal sensing device according to an embodiment of the present disclosure may include first and second electrodes 10 and 20, an insulating unit 30, and a controller 40.

The first electrode 10 may be provided in a ring shape, may be formed of a conductor, and may be worn on the finger of a user to be in contact with the finger.

The second electrode 20 may be assembled on the outside of the first electrode 10, may be formed of a conductor, and may come into contact with the body of the user.

The insulating unit 30 may be disposed between the first electrode 10 and the second electrode 20 to maintain insulation between the first electrode 10 and the second electrode 20. A biometric sensor may be provided at one side of the insulating unit 30.

The biometric sensor may measure a biometric signal such as an electrocardiogram (ECG) and photoplethysmography (PPG).

Blood pressure may be monitored and managed in real time using such a biometric signal, thereby contributing to prevention of hypertension.

The controller 40 may be disposed between the first electrode 10 and the second electrode 20, and may collect a biometric signal when the second electrode 20 comes into contact with the body of the user except for the finger.

The second electrode 20 may be configured in an arc shape and a top cover 50 may be provided at one side of the second electrode 20.

The second electrode 20 may be assembled near a side of the first electrode 10 or the insulating unit 30, and the top cover 50 may be assembled on an opposite side.

A printed circuit board 60 and a battery 70 may be mounted inside the second electrode 20.

The printed circuit board 60 may be formed of a flexible material, and the controller 40 may be mounted thereon.

A communication module for communication with an external electronic device may be mounted on the printed circuit board 60.

The battery 70 may supply power to the first and second electrodes 10 and 20 to cause current to flow therein and may supply power to the printed circuit board 60 as well as the controller 40.

The ring-shaped biometric signal sensing device according to an embodiment of the present disclosure as configured above may be worn on the finger of the user.

A biometric signal may be detected by placing the ring-shaped biometric signal sensing device according to an embodiment of the present disclosure on any one part of the body while the user puts the ring-shaped biometric signal sensing device on his or her finger.

In more detail, minute current may be generated while the heart is beating, and the intensity of the minute current changes over time, and in this regard, information on the intensity of the current, etc. may be transferred to the controller 40 through the first electrode 10 or the second electrode 20, and the controller 40 may collect and store the received information on the current change.

The collected current change may be represented in an electrocardiogram graph over time, and a health status, etc. of the heart may be analyzed by analyzing the characteristics of the electrocardiogram graph.

The electrocardiogram graph may include P wave, QRS wave (QRS group, QRS complex), T wave, and U wave. The blood pressure sensor may secure a biometric signal such as blood pressure and pulse transferred through the blood vessels of the finger.

That is, the ring-shaped biometric signal sensing device according to an embodiment of the present disclosure may detect a biometric signal such as an electrocardiogram, blood pressure, and a pulse.

The ring-shaped biometric signal sensing device according to an embodiment of the present disclosure may minimize wearing discomfort by providing an external size that is ultra-compact enough to be worn on the finger.

The controller 40 of the ring-shaped biometric signal sensing device according to an embodiment of the present disclosure may include a communication module that is connected to a communication terminal to transmit data of the biometric signal.

The communication terminal may be a smartphone, a tablet PC, a laptop computer, a desktop, an electronic device connected to a network, etc.

The communication terminal may be a communication component for implementing wired communication or wireless communication.

Thus, the user may usually collect and store biometric signals and may then transmit the collected data to the communication terminal or may contact a designated medical service and transmit the data thereto. A medical institution may diagnose physical health of the user by examining the data of the user's biometric signal received through the communication terminal or the medical service.

That is, it may be convenient for the user to continuously collect and store biometric signals during daily life, and a doctor may diagnose disease based on more data to significantly improve the accuracy of diagnosis.

The controller 40 of the ring-shaped biometric signal sensing device according to an embodiment of the present disclosure may detect the biometric signal of the user or may transmit the collected data when the user repeats contact and release of the second electrode 20 once or twice in a row.

That is, when the user does not stimulate the second electrode 20, the controller 40 may stop operating, and when the user stimulates the second electrode 20, the controller 40 may operate according to a signal of the stimulation.

In response to the stimulus, for example, if an action such as tapping the second electrode 20 is performed twice in a row, it may be understood that an electrocardiogram signal and a pulse wave signal are collected.

If there is no external stimulus for a set period of time, the ring-shaped biometric signal sensing device according to an embodiment of the present disclosure may switch to a power saving state to prevent battery power from being consumed.

The electrocardiogram sensor ring according to an embodiment of the present disclosure may be provided in various ways with different inner diameters, and for example, may be provided in 7 types for each size.

According to another aspect, the insulating unit 30 may be formed of a flexible material, and a portion of the insulating unit 30 may be placed through the first electrode 10 to be in close contact with the finger of the user. The first electrode 10 may include a hole formed therethrough, and the insulating unit 30 may include an inwardly protruding protrusion, and the protrusion may be inserted into the hole such that an inner edge of the protrusion is aligned with an inner edge of the hole viewed from an inside of the first electrode 10.

The flexible material may be silicon or a rubber material, and thus when the finger is inserted into the first electrode 10, a portion of the insulating unit 30 may protrude inwards to be in close contact with the finger, and thus the first electrode 10 may be in stronger and more reliable contact with the skin of the finger.

That is, the ring-shaped biometric signal sensing device according to the embodiment of the present disclosure may improve the reliability of the collected biometric signal by minimizing an error when the first electrode 10 is securely attached to the finger of the user to secure the biometric signal.

Figure 4:
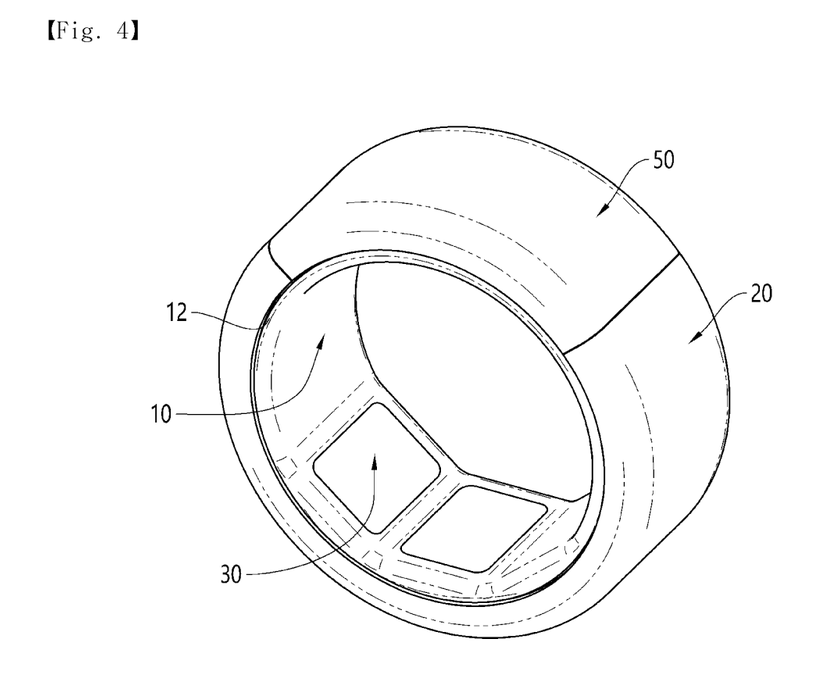
FIG. 4 is a diagram for explaining a ring-shaped biometric signal sensing device according to another embodiment of the present disclosure.
Figure 5:
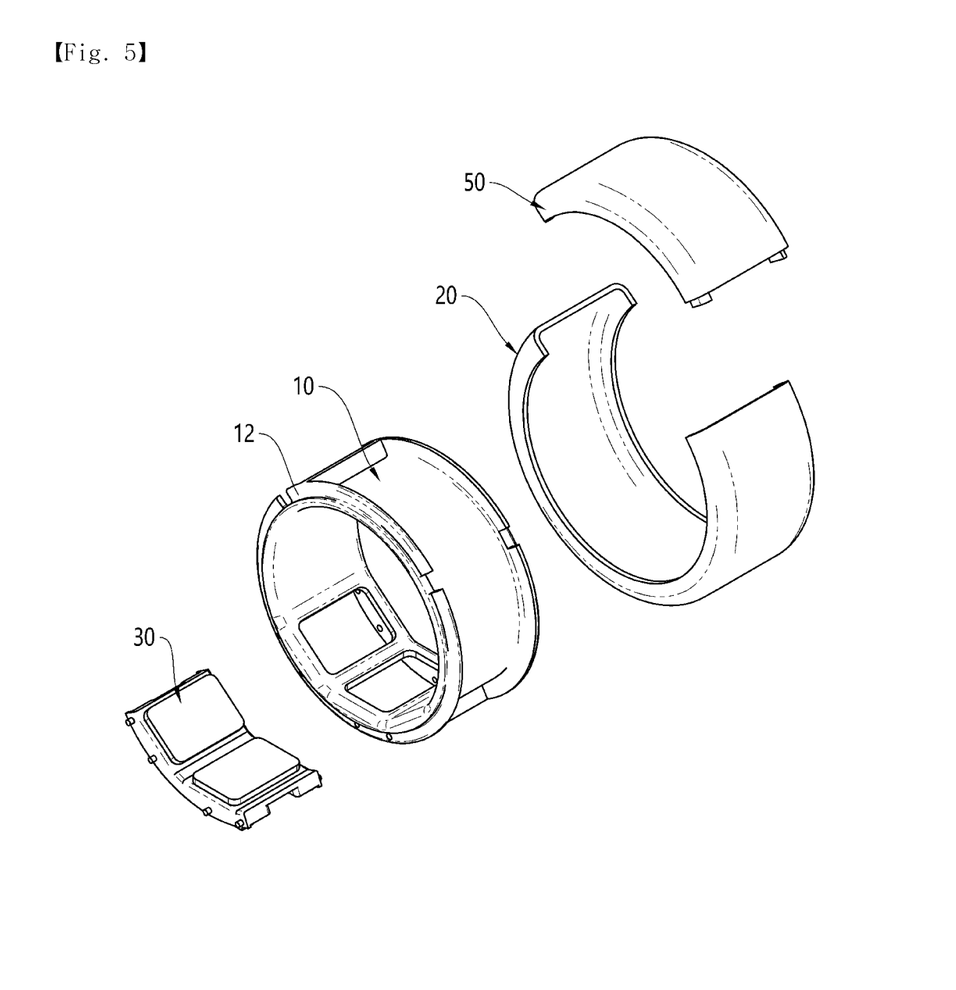
FIG. 5 is an exploded diagram for explaining main components of a ring-shaped biometric signal sensing device according to another embodiment of the present disclosure.
Figure 6:
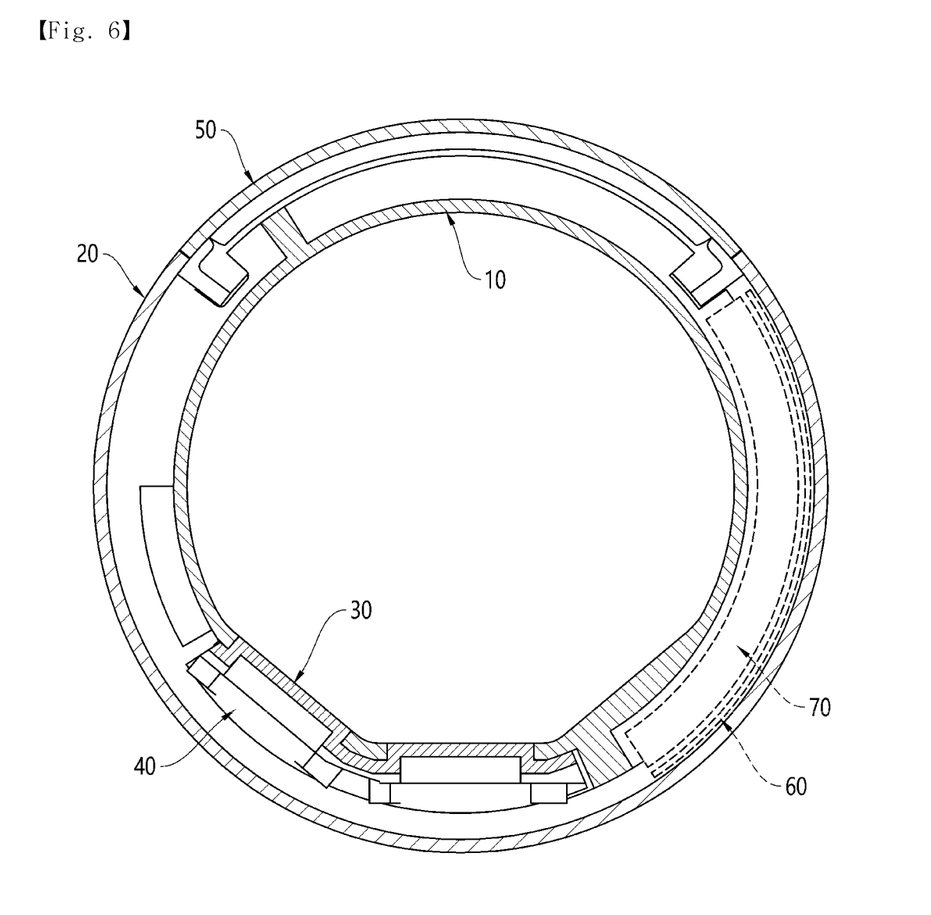
FIG. 6 is a cross-sectional view for explaining the internal configuration of a ring-shaped biometric signal sensing device according to another embodiment of the present disclosure.

Hereinafter, a ring-shaped biometric signal sensing device according to another embodiment of the present disclosure will be described with reference to FIGS. 4 to 6. FIG. 4 is a diagram for explaining a ring-shaped biometric signal sensing device according to another embodiment of the present disclosure. FIG. 5 is an exploded diagram for explaining main components of a ring-shaped biometric signal sensing device according to another embodiment of the present disclosure. FIG. 6 is a cross-sectional view for explaining the internal configuration of a ring-shaped biometric signal sensing device according to another embodiment of the present disclosure.

The ring-shaped biometric signal sensing device according to another embodiment of the present disclosure may be configured by further installing the second electrode 20 at the first electrode 10 in the ring-shaped biometric signal sensing device according to the aforementioned embodiment of the present disclosure.

As shown in FIG. 5, the rim 12 may be formed at an outer periphery of the first electrode 10 and an insulating layer may be formed on the rim 12.

That is, when the first electrode 10 is assembled on the outside of the second electrode 20, the first electrode 10 and the second electrode 20 may be insulated from each other through the insulating layer. Further, as shown in FIGS. 5 and 6, the first electrode 10 may include two holes formed therethrough, and the insulating unit 30 may include two inwardly protruding protrusions, and the protrusions may be inserted into the holes such that the inner edges of the protrusions are aligned with the inner edges of the holes viewed from an inside of the first electrode 10. The insulating layer may be formed by depositing tin to form a UV coating layer, and the coating layer may be 0.1 mm thick.

As described above, the thickness and external size of the ring-shaped structure may be minimized by assembling the first electrode 10 and the second electrode 20 to be in direct contact with each other.

The first and second electrodes 10 and 20 may be formed of stainless steel or conductive nanoparticles and may be coated with gold, silver, etc. Accordingly, the user may feel as though they were wearing a gold ring or a silver ring to minimize a sense of unfamiliarity experienced by the user and may conduct electricity well with the body.

The first electrode 10 may be molded together with the insulating unit 30 through insert injection, and the controller 40 may be disposed within the insulating unit 30

As shown in FIG. 6, the printed circuit board 60 and the battery 70 may be mounted within the second electrode 20.

Although embodiments of the present disclosure have been described above with reference to the accompanying drawings, it should be understood that those skilled in the art to which the present disclosure pertains can implement the present disclosure in other specific forms without changing the technical spirit or essential features thereof.

Therefore, it should be understood that the embodiments described above are illustrative and not restrictive in all respects, and the scope of the present disclosure is defined by the following claims, all changes or modifications derived from derived from meaning and scope of the claims and their equivalents should be construed as being included in the scope of the present disclosure.

INDUSTRIAL AVAILABILITY

A ring-shaped biometric signal sensing device according to an embodiment of the present disclosure may be worn on the finger of a user and may contact the body of the user to measure an electrocardiogram, a pulse, blood pressure, etc.

The invention claimed is:

1. A ring-shaped biometric signal sensing device comprising:
a first electrode having a ring shape and a conductor, the first electrode being configured to be worn on a finger of a user and to be in contact with the finger;
a second electrode disposed on an outside of the first electrode, having a conductor, and configured to be in contact with a body of the user;
an insulating unit disposed between the first electrode and the second electrode to maintain insulation between the first electrode and the second electrode; and
a controller disposed in the insulating unit, including a biometric sensor, and configured to collect a biometric signal when the second electrode comes into contact with the body of the user,
wherein the insulating unit has a flexible material, and a portion of the insulating unit penetrates the first electrode and is configured to be in close contact with the finger of the user when worn by the user, and
wherein the controller is configured to collect the biometric signal of the user when the second electrode contacts and releases contact with a portion of the body of the user other than the finger once or twice in a row.

2. The ring-shaped biometric signal sensing device of claim 1, wherein the biometric signal has at least one of an electrocardiogram signal, a blood pressure signal, or a pulse signal or a combination thereof.

3. The ring-shaped biometric signal sensing device of claim 1, wherein the controller comprises a communication module connected to a communication terminal and configured to transmit data of the biometric signal.

4. The ring-shaped biometric signal sensing device of claim 1, wherein a rim is disposed at an outer periphery of the first electrode, an insulating layer is disposed on the rim, the insulating layer being configured to insulate the first electrode and the second electrode from each other.

5. The ring-shaped biometric signal sensing device of claim 1, wherein:
the first electrode has a hole;
the insulating unit has a protrusion protruding inwards,
wherein the protrusion is disposed in and through the hole and an edge of the protrusion is aligned with an edge of the hole.

6. The ring-shaped biometric signal sensing device of claim 5, wherein:
a surface of the protrusion has a flat surface shape; and
a flat surface of the protrusion is configured to be in close contact with the finger of the user.

7. The ring-shaped biometric signal sensing device of claim 6, wherein the first electrode has two holes and the insulating unit has two protrusions.

8. A ring-shaped biometric signal sensing device comprising:
a first electrode having a ring shape and a conductor, the first electrode being configured to be worn on a finger of a user to be in contact with the finger;
a second electrode disposed on an outside of the first electrode, having a conductor, and configured to be in contact with a body of the user;
an insulating unit disposed between the first electrode and the second electrode to maintain insulation between the first electrode and the second electrode; and
a controller disposed in the insulating unit, including a biometric sensor, and configured to collect a biometric signal when the second electrode comes into contact with the body of the user,
wherein the controller is configured to collect the biometric signal of the user when the second electrode contacts and releases contact with a portion of the body of the user other than the finger once or twice in a row.

9. A ring-shaped biometric signal sensing device comprising:
a first electrode having a ring shape and a conductor, the first electrode being configured to be worn on a finger of a user and to be in contact with the finger;
a second electrode disposed on an outside of the first electrode, having a conductor, and configured to be in contact with a body of the user;
an insulating unit disposed between the first electrode and the second electrode to maintain insulation between the first electrode and the second electrode; and
a controller disposed in the insulating unit, including a biometric sensor, and configured to collect a biometric signal when the second electrode comes into contact with the body of the user,
wherein the insulating unit has a flexible material, and a portion of the insulating unit penetrates the first electrode and is configured to be in close contact with the finger of the user when worn by the user,
wherein the first electrode has a hole, and the insulating unit has a protrusion protruding inwards,
wherein the protrusion is disposed in and through the hole and an edge of the protrusion is aligned with an edge of the hole,
wherein a surface of the protrusion has a flat surface shape, and a flat surface of the protrusion is configured to be in close contact with the finger of the user, and
wherein the first electrode has two holes and the insulating unit has two protrusions.

\* \* \* \* \*